(12) United States Patent
Scates

(10) Patent No.: US 8,168,822 B2
(45) Date of Patent: May 1, 2012

(54) ACETIC ACID PRODUCTION BY WAY OF CARBONYLATION WITH ENHANCED REACTION AND FLASHING

(75) Inventor: Mark O. Scates, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 414 days.

(21) Appl. No.: 12/459,725

(22) Filed: Jul. 7, 2009

(65) Prior Publication Data

US 2011/0009665 A1    Jan. 13, 2011

(51) Int. Cl.
*C07C 51/12* (2006.01)
(52) U.S. Cl. ...................................................... 562/519
(58) Field of Classification Search .................. None
See application file for complete search history.

(56) References Cited

U.S. PATENT DOCUMENTS

| | | | |
|---|---|---|---|
| 5,001,259 A | 3/1991 | Smith et al. | 562/519 |
| 5,026,908 A | 6/1991 | Smith et al. | 562/519 |
| 5,144,068 A | 9/1992 | Smith et al. | 562/519 |
| 5,416,237 A | 5/1995 | Aubigne et al. | 562/519 |
| 5,529,970 A | 6/1996 | Peng | 502/400 |
| 5,696,284 A | 12/1997 | Baker et al. | 560/232 |
| 5,770,768 A | 6/1998 | Denis et al. | 562/519 |
| 5,877,347 A | 3/1999 | Ditzel et al. | 562/519 |
| 5,877,348 A | 3/1999 | Ditzel et al. | 562/519 |
| 5,883,295 A | 3/1999 | Sunley et al. | 562/519 |
| 5,932,764 A | 8/1999 | Morris et al. | 562/519 |
| 5,942,460 A | 8/1999 | Garland et al. | 502/150 |
| 6,322,612 B1 | 11/2001 | Sircar et al. | 95/97 |
| 6,627,770 B1 | 9/2003 | Cheung et al. | 562/519 |
| 6,657,078 B2 | 12/2003 | Scates et al. | 562/519 |
| 2005/0165251 A1 * | 7/2005 | Muskett | 562/519 |

FOREIGN PATENT DOCUMENTS

| | | |
|---|---|---|
| CN | ZL92108244.4 | 6/1999 |
| CN | ZL 94100505.4 | 6/2000 |
| CN | 1345631 | 4/2002 |
| CN | 1349855 | 5/2002 |
| CN | 1651388 | 7/2007 |
| EP | 0 161 874 A1 | 11/1985 |
| EP | 0 685 446 A1 | 12/1995 |
| EP | 0 759 419 A1 | 2/1997 |
| EP | 0 849 248 A1 | 6/1998 |

OTHER PUBLICATIONS

"Process of 200ktpa Methanol Low Press Oxo Synthesis AA" (SWRDICI 2006) (China).
International Search Report and Written Opinion, Jun. 2011.

* cited by examiner

*Primary Examiner* — Daniel Sullivan
*Assistant Examiner* — Yevegeny Valenrod
(74) *Attorney, Agent, or Firm* — Michael W. Ferrell

(57) ABSTRACT

A method of making acetic acid includes: (a) catalytically reacting methanol or a reactive derivative thereof with carbon monoxide in the presence of a homogeneous Group VIII metal catalyst and a methyl iodide promoter in a reactor vessel in a liquid reaction mixture including acetic acid, water, methyl acetate, methyl iodide and homogeneous catalyst, the reactor vessel being operated at a reactor pressure; (b) withdrawing reaction mixture from the reaction vessel and feeding the withdrawn reaction mixture along with additional carbon monoxide to a pre-flasher/post reactor vessel operated at a pressure below the reactor vessel pressure; (c) venting light ends in the pre-flasher vessel and concurrently consuming methyl acetate in the pre-flasher/post reactor vessel. Reaction conditions, residence time and composition are controlled in the pre-flasher/post reactor vessel such that a pre-flash mixture is enriched in acetic acid and diminished in methyl iodide and methyl acetate in the pre-flasher/post reactor vessel. From the pre-flasher/post reaction vessel the acetic acid enriched mixture is (d) withdrawn and fed to a flash vessel.

24 Claims, 1 Drawing Sheet

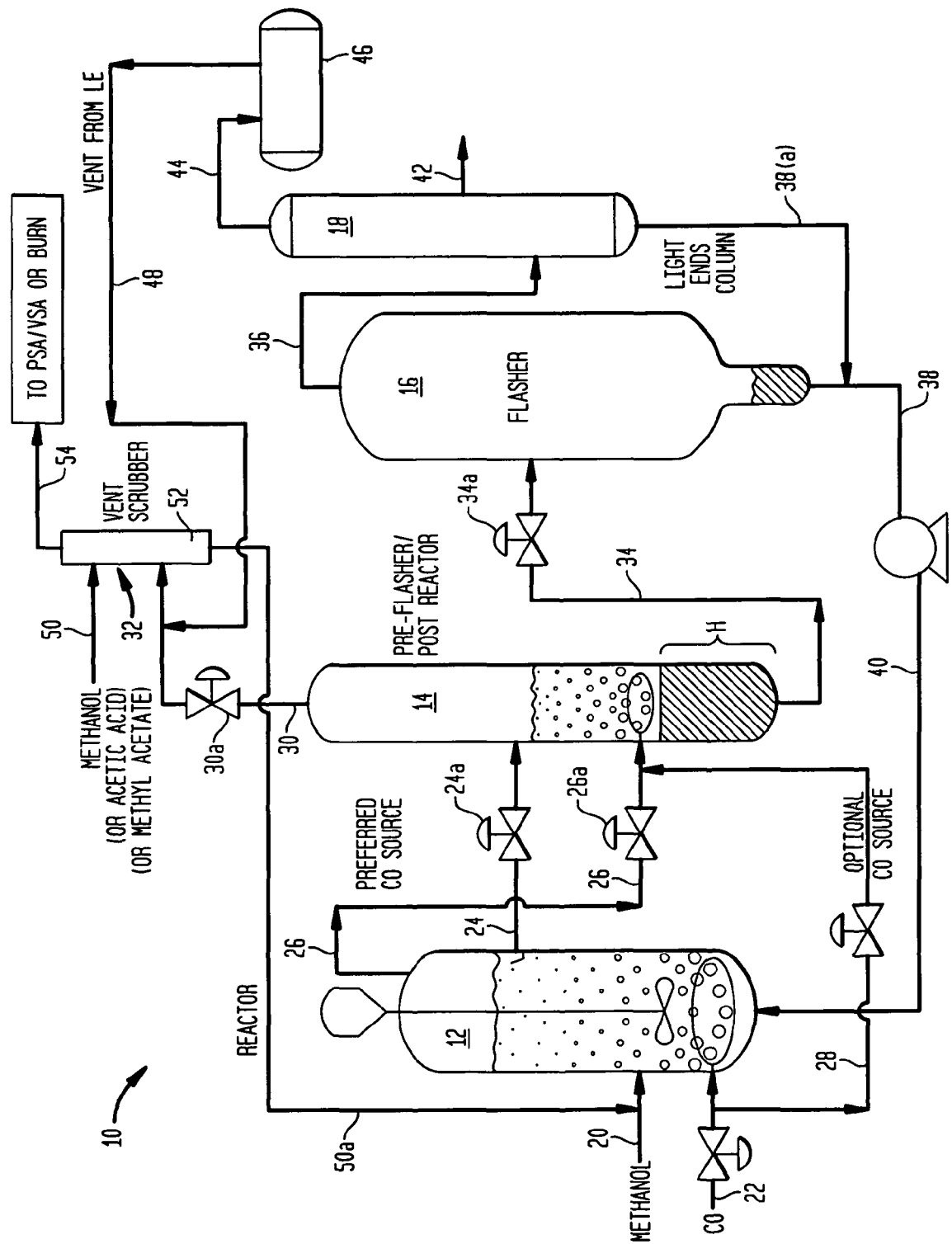

ACETIC ACID PRODUCTION BY WAY OF CARBONYLATION WITH ENHANCED REACTION AND FLASHING

TECHNICAL FIELD

The present invention relates to acetic acid production and, in particular, to a methanol carbonylation system having an intermediate pressure, pre-flash/post reactor vessel that removes methyl iodide and consumes methyl acetate prior to flashing in a low pressure flasher. A low pressure absorber debottlenecks the light ends column of the purification train.

BACKGROUND OF THE INVENTION

Among currently employed processes for synthesizing acetic acid, one of the most used commercially is the catalyzed carbonylation of methanol with carbon monoxide. Preferred methods of practicing this technology include so-called "low water" processes catalyzed with rhodium or iridium of the class seen in U.S. Pat. No. 5,001,259, issued Mar. 19, 1991; U.S. Pat. No. 5,026,908, issued Jun. 25, 1991; and U.S. Pat. No. 5,144,068, issued Sep. 1, 1992; as well as European Patent No. EP 0 161 874 B2, published Jul. 1, 1992. The features involved in practicing a low water carbonylation process may include maintaining in the reaction medium, along with a catalytically effective amount of rhodium and at least a finite concentration of water, an elevated concentration of inorganic iodide anion over and above the iodide ion that is present due to hydrogen iodide in the system. This iodide ion may be a simple salt, with lithium iodide being preferred in most cases. U.S. Pat. Nos. 5,001,259, 5,026,908, 5,144,068 and European Patent No. EP 0 161 874 B2 are herein incorporated by reference.

Generally speaking, a methanol carbonylation production line includes a reaction section, a purification section, light ends recovery and a catalyst reservoir system. In the reaction section, methanol and carbon monoxide are contacted with a rhodium or iridium catalyst in a homogenous stirred liquid phase reaction medium in a reactor to produce acetic acid. Methanol is pumped into the reactor from a methanol surge tank. The process is highly efficient, having a conversion of methanol to acetic acid of typically greater than 99 percent. The reaction section also generally includes a flash vessel coupled to the reactor which flashes a draw stream in order to remove crude product from the reaction section. The crude product is fed to a purification section which includes generally a light ends or stripper column, a drying column, auxiliary purification and optionally a finishing column. In the process, various uncondensible vent streams containing light ends, notably methyl iodide, carbon monoxide and methyl acetate are generated and fed to the light ends recovery section. These vent streams are scrubbed with a solvent to remove the light ends which are returned to the system or discarded.

Despite advances in the art, catalyst deactivation and vent losses, especially carbon monoxide losses, remain persistent inefficiencies in methanol carbonylation systems. So also, there is always a need to reduce capital and operating expense associated with vent scrubbing and product purification.

In a traditional methanol carbonylation plant, a high pressure and low pressure absorber are included wherein acetic acid is used as the scrubber solvent. The acetic acid solvent must subsequently be stripped of light ends, usually in another purification column so that the acid is not wasted. Such columns are expensive because they must be made of a highly corrosion resistant material such as zirconium alloys and so forth. Moreover, stripping light ends from the acid requires steam and contributes to operating expense. Methanol has been suggested for use as a scrubber solvent in connection with a methanol carbonylation processes as well. In this regard, see U.S. Pat. No. 5,416,237 to Aubigne et al., entitled "Process for the Production of Acetic Acid". It is noted in the '237 patent that noncondensibles from a flash tank vapor overhead may be scrubbed countercurrently with chilled methanol. The methanol scrubber solvent residual stream is added to pure methanol and then used as feed to the reactor. See Col. 9, lines 30-42. Chinese Patent Application Publication No. 200410016120.7 discloses a method for recovering light components in vent gas from production of acetic acid/acetic anhydride by way of scrubbing with methanol and acetic acid. Another system is seen in an industrial publication entitled "Process of 200 ktpa Methanol Low Press Oxo Synthesis AA" (SWRDICI 2006) (China) (referred to as SWRDICI below). In this research publication, there is shown a vent gas treatment system including a high pressure absorber as well as a low pressure absorber. Both absorbers of this system are described as being operated utilizing methanol as a scrub fluid.

European Patent No. EP 0 759 419 proposes to reduce vent losses by injecting methanol into the reactor vent stream and catalytically producing more product in a secondary reactor, which optionally contains heterogeneous catalyst.

Catalyst deactivation and loss is generally believed due to carbon monoxide-depleted or low pressure environments in the carbonylation system as are seen in the flasher. As carbon monoxide levels fall in the catalyst solution, rhodium increasingly takes the form of rhodium triiodide which precipitates. Various modifications have been proposed in the art to address this aspect of conventional processes, perhaps the most successful being the use of lithium iodide to enhance catalyst stability and reaction rates under low water conditions. Other proposed modifications are discussed below.

U.S. Pat. No. 5,770,768 to Denis et al. discloses carbonylation systems where recycle catalyst solution from the flasher is treated with additional carbon monoxide prior to return to the reactor to increase catalyst stability.

A high pressure "converter" reactor is proposed in Chinese Patent No. ZL92108244.4 as well as SWRDICI (noted above). The converter reactor illustrated in SWRDICI is coupled to the high pressure vent scrubber and is reported to allow the reaction to proceed to a greater extent prior to flashing.

In accordance with the present invention, there is provided an improved carbonylation system with staged reaction and pre-flash removal of light ends to increase productivity and operating efficiencies.

SUMMARY OF THE INVENTION

There is provided in accordance with this invention a method of making acetic acid comprising: (a) catalytically reacting methanol or a reactive derivative thereof with carbon monoxide in the presence of a homogeneous Group VIII metal catalyst and a methyl iodide promoter in a reactor vessel containing a liquid reaction mixture including acetic acid, water, methyl acetate, methyl iodide and homogeneous catalyst, the reactor vessel being operated at a reactor pressure; (b) withdrawing reaction mixture from the reaction vessel and feeding the withdrawn reaction mixture along with additional carbon monoxide to a pre-flasher/post reactor vessel operated at a reduced pressure below the reactor vessel pressure; (c) venting light ends in the pre-flasher vessel and concurrently consuming methyl acetate in the pre-flasher/ post reactor vessel. Reaction conditions, residence time and composition are controlled in the pre-flasher/post reactor vessel such that a pre-flash mixture is enriched in acetic acid and diminished in methyl iodide and methyl acetate while in the pre-flasher/post reactor vessel as compared with the reaction mixture. There is (d) withdrawn from pre-flasher/post reactor vessel, the acetic acid enriched mixture, which is fed to a flash vessel; wherefrom there is (e) flashed a crude acetic acid stream from the reaction mixture. The flash vessel is operated at a pressure below the pressure of the pre-flasher/post reactor vessel. The process also includes (f) recycling residue from the flash vessel to the reactor vessel; and (g) purifying the crude product stream.

Advantages of the inventive system include increased productivity, de-bottlenecking of the light ends column and optionally increasing carbon monoxide efficiency as well as enhancing catalyst stability.

The pre-flasher/post reactor vessel is suitably operated at a pressure of at least 5 or 10 psi lower than the pressure of the reaction vessel, preferably at least 15 psi lower than the pressure of the reactor vessel. In some embodiments the pre-flasher/post reactor vessel is operated at a pressure of at least 20 psi, 25 psi or 30 psi lower than the pressure of the reactor vessel.

Supplemental sparging of carbon monoxide to consume methyl acetate in the pre-flasher/post reactor vessel is preferred.

Further details and advantages of the present invention will become apparent from the discussion which follows.

BRIEF DESCRIPTION OF THE DRAWINGS

The invention is described in detail below with reference to the appended drawing, wherein like numerals designate similar parts. In the drawing:

FIG. 1 is a schematic diagram illustrating a carbonylation system for making acetic acid in accordance with the invention.

DETAILED DESCRIPTION OF THE INVENTION

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. Percent, % and like terms refer to weight percent, unless otherwise indicated.

An "iodide salt stabilizer/co-promoter" and like terminology refers to components which generate and maintain elevated levels of iodide anions, that is, over and above levels attributable to hydriodic acid. The iodide salt stabilizer/co-promoter may be a simple salt or any compound or component that generates and maintains iodide anion in the reaction mixture as is further discussed herein.

"Light ends" refers to components having a boiling point lower than acetic acid. Thus, methyl iodide, methyl acetate and dissolved carbon monoxide are "light ends" for present purposes.

"Low pressure" and like terminology refers to pressures lower than the pressure maintained in a carbonylation reactor of the class discussed herein. A "reduced" pressure is usually at least 5 psi lower than a referenced pressure, preferably at least 10 psi or 20 psi lower than a referenced pressure. A "low pressure" absorber refers to an absorber operated at a pressure substantially lower than the reactor pressure, preferably more than 25 psi lower than the pressure maintained in the carbonylation reactor.

When referring to a reduction in methyl acetate due to consumption thereof in the pre-flasher/post reactor vessel at specific levels, the percentage reduction is relative to the amount of methyl acetate in the reaction mixture in the reactor. Thus, a 25% reduction of methyl acetate in the pre-flasher/post reactor refers to a level 25% lower in the outlet stream of the pre-flasher/post reactor as compared to the level maintained in the reactor vessel. Thus, when the level of methyl acetate is 4 wt. % in the reactor vessel and methyl acetate is consumed in the pre-flasher/post reactor vessel to a level of 3%, a 25% reduction is achieved. In some preferred aspects of the invention, methyl acetate is consumed to a level of less than 1.5 wt. % or less than 1 wt. % in the reaction mixture exiting the pre-flasher/post reactor. In still other cases, the concentration of methyl acetate in the stream existing the pre-flasher/post reactor may be less than 0.5 wt. % or less than 0.25 wt. %

In a conventional carbonylation reactor, vent gas comprising hydrogen, carbon dioxide, and carbon monoxide is fed from the reactor to a high-pressure absorber operated at pressures similar to those in the reactor to recover reactants and/or product. Acetic acid is separated from a catalyst solution in a flasher. Methyl iodide and methyl acetate accompanying the crude acetic acid product is removed in a light ends column and condensed or scrubbed out of vent gas with an absorber.

In the process according to the invention, vent gas from a primary reactor may be fed directly to a pre-flasher/post reactor vessel, thereby conserving carbon monoxide reactant while reducing or eliminating the need for a high-pressure absorber. Additional carbon monoxide provided to the reaction mixture stabilizes the catalyst and reacts with methyl acetate to increase acetic acid productivity of the system.

The pre-flasher/post reactor vessel is operated at a pressure intermediate between the operating pressures of the primary reactor and a subsequent flasher, thereby retaining most of the product acetic acid in solution, while flashing off methyl iodide and methyl acetate. The methyl iodide and methyl acetate flashed off from the pre-flasher/post reactor vessel reactor may be fed to a condenser or may be sent directly to a low-pressure absorber, thereby reducing the load on a subsequent light-ends column. Operation of an absorber is generally more expensive than operation of condensing unit. Therefore, minimizing the need for absorption results in a reduction of operating costs.

The reaction liquid is typically drawn from the reactor and flashed in a staged or multi-step process using a pre-flasher/post reactor vessel as well as a traditional flash vessel as hereinafter described. The crude vapor process stream from the flasher is sent to a purification section which generally includes at least a light ends column and a dehydration column as is known in the art.

The present invention is further appreciated by reference to FIG. 1 which is a schematic diagram illustrating a typical carbonylation process and apparatus according to an embodiment of the invention.

There is shown in FIG. 1a carbonylation apparatus 10 constructed in accordance with the present invention. Apparatus 10 includes, generally, a carbonylation reactor 12, a pre-flasher/post reactor vessel 14, a flasher 16, as well as additional purification such as a light ends stripper column 18, and so forth as will be appreciated by one of skill in the art.

In operation, methanol and carbon monoxide are fed to reactor vessel 12 by way of lines 20, 22 respectively for reaction in the catalytic reaction medium contained in reactor 12. The carbonylation reaction proceeds in a homogeneous catalytic reaction system comprising a reaction solvent (typically acetic acid), methanol and/or its reactive derivatives, a soluble rhodium catalyst, methyl iodide, methyl acetate and at least a finite concentration of water. Methanol and carbon monoxide efficiencies are generally greater than about 98 and 90% respectively, as will be appreciated from U.S. Pat. Nos. 5,001,259; 5,026,908; and 5,144,068, all to Smith et al., the disclosures of which are hereby incorporated by reference.

From reactor 12, a portion of the reaction medium is fed forward via line 24 through a pressure-reducing value 24a to pre-flasher/post reactor 14. There is also provided via line 26, carbon monoxide by way of vent from reaction vessel 12 to pre-flasher 14 as shown. A preferred source of CO is from vent 26 through a pressure-reducing valve 26a inasmuch as this reduces the need to supply additional fresh carbon monoxide to pre-flasher/post reactor 14 which may be accomplished, for example, via line 28 as shown toward the lower portion of the diagram. Note that carbon monoxide is sparged into vessel 14 at a disengaging height H above the bottom of vessel 14 and line 34 in order to prevent (or reduce the amount of) carbon monoxide from being drawn into line 34. Height H may be at least 0.25 meter or more, preferably at least 0.5 meter, or at least 1 meter.

In pre-flasher/post reactor 14 the reaction medium is held at intermediate pressure while the CO interacts with the reaction mixture and consumes methyl acetate. In a preferred embodiment, the amount of carbon monoxide added to vessel 14 and the reaction conditions are controlled such that the methyl acetate in the reaction mixture is substantially consumed prior to further processing. Pre-flasher/post reactor 14 is provided with a vent at 30 to remove gases from the system including noncondensibles as well as methyl iodide and optionally some methyl acetate to low pressure scrubbing system 32 as indicated in the diagram. Prior to feeding to the low pressure absorption system 32, the pressure in the vent stream 30 is lowered by passing the stream through a pressure-reducing valve indicated at 30a.

The reaction mixture is thus modified and pre-conditioned prior to flashing. In particular, a portion of the methyl iodide and optionally a portion of methyl acetate are removed from the reaction mixture and provided to the low pressure vent scrubbing system prior to flashing at low pressure. In this way, purification requirements for the crude product will be reduced as will be appreciated from the discussion which follows. Following reaction in the pre-flasher/post reactor vessel 14, the conditioned reaction mixture, now depleted of light ends, is fed forward via line 34 through a pressure-reducing valve 34a to flasher 16. In flasher 16, the pressure is reduced with respect to pre-flasher 14 which in turn is reduced with respect to the reactor 12. In flasher 16, crude acetic acid is flashed from the reaction mixture and exits as overhead indicated at 36 and is supplied to a light ends column 18 as is known in the art.

From flasher 16, the catalyst is recycled via lines 38, 40 to reactor 12 as is also known in the art.

The crude product fed to light ends column 18 via line 36 has much reduced levels of methyl iodide and methyl acetate as compared with a conventional carbonylation system because the methyl acetate has been consumed in the pre-flasher/post reactor vessel 14 and the methyl iodide and optionally methyl acetate have been pre-flashed, to low pressure vent scrubber system 32 as shown in the diagram. From light ends column 18, the product is fed forward in a purified stream 42 with most of the methyl iodide and methyl acetate removed from the product. Stream 42 is fed forward to a dehydration column to remove water from the product stream and is subsequently optionally processed to remove other impurities, such as heavy ends, organic iodides, before storage and shipping. The residue from column 18 is recycled via line 38a to line 38 and 40 and eventually to reactor 12.

The overhead from column 18 is condensed and exits via 44 to receiver 46 and may be recycled as is known in the art. Non-condensibles, i.e., at 48 are fed to the low pressure vent scrubbing system, which may utilize methanol and/or acetic acid and/or methyl acetate as shown at 50. In this regard, there is provided an absorption tower 52. When methanol is used as the scrub fluid in the low pressure scrubber, the spent scrub fluid may be fed directly to reactor 12 via line 50a as shown in the diagram. Preferably, more than 90% or 95% of the methyl iodide is removed from the vent gas by the absorbent fluid prior to additional processing. The scrubber fluid is generally chilled to a temperature of from about 5° C. to about 25° C. prior to use in the tower, with the proviso that when acetic acid is used as the scrubber solvent, the temperature of the solvent is held at 17° C. or more to prevent freezing.

The non-condensibles, including carbon monoxide from tower 52 exit via line 54 and may be further purified by pressure swing adsorption or vacuum swing adsorption as is known in the art. In this regard, there is provided description of these processes in U.S. Pat. No. 5,529,970 to Peng and U.S. Pat. No. 6,322,612 to Sircar et al., the disclosures of which are incorporated herein by reference.

A high pressure absorber is not required in the embodiment illustrated in FIG. 1, saving capital and operating costs. In other embodiments, use of a high pressure absorber can be minimized, reducing operating costs.

It will be appreciated from the foregoing that lower methyl iodide and methyl acetate levels in the resulting flashed crude product stream 36 debottlenecks the light ends column. High gas sparge rates can be achieved without losing carbon monoxide because of carbon monoxide consummation in pre-flasher/post reactor 14.

Carbonylation system 10 optionally uses only two primary purification columns and is preferably operated as described in more detail in U.S. Pat. No. 6,657,078 to Scates et al., entitled "Low Energy Carbonylation Process", the disclosure of which is incorporated herein by reference. Additional columns are generally used as desired, depending on the system.

A Group VIII catalyst metal used in connection with the present invention may be a rhodium and/or iridium catalyst. The selection of catalyst is not critical to the operation of the present invention. In the event that a rhodium-based catalyst is selected, the rhodium metal catalyst may be added in any suitable form such that rhodium is in the catalyst solution as an equilibrium mixture including $[Rh(CO)_2I_2]^-$ anion, as is well known in the art. When rhodium solution is in the carbon monoxide-rich environment of the reactor, solubility of the rhodium is generally maintained because rhodium/carbonyl iodide anionic species are generally soluble in water and acetic acid. However, when transferred to carbon monoxide depleted environments as typically exist in the flasher, light ends column and so forth, the stability of the rhodium/catalyst composition is reduced since less carbon monoxide is available. A significant amount of rhodium precipitates as $RhI_3$, for example, and is lost in conventional systems; details as to the form of entrained rhodium downstream of the reactor are not well understood. Iodide salt stabilizer/co-promoters help alleviate precipitation in the flasher under so-called "low water" conditions as will be appreciated by one of skill in the art. A rhodium catalyst may be present with a concentration in the range of from 1 ppm up to the range of solubility, preferably in the range of from 10 to 2000 ppm by weight of rhodium.

Iodide salt stabilizer/co-promoters used in connection with this invention may be in the form of a soluble salt of an alkali metal or alkaline earth metal or a quaternary ammonium or phosphonium salt. In certain embodiments, the catalyst stabilizer/co-promoter is lithium iodide, lithium acetate, or mixtures thereof. The iodide salt may be added as a mixture of salts such as a mixture of lithium iodide and sodium iodide and/or potassium iodide. See U.S. Pat. Nos. '259; '908; and '068, all to Smith et al., as referred to above. Alternatively, the iodide salt stabilizer/co-promoter may be added as a salt precursor which generates iodide anion in-situ since under the operating conditions of the reaction system. A wide range of non-iodide salts which are useful as precursors include alkali metal acetates and carboxylates which will react with methyl iodide and/or HI to generate the corresponding iodide salt stabilizer. Suitable iodide salts may likewise be generated in situ from non-ionic precursors, such as a phosphine oxide, arsenes, phosphines, amines, amino acids, sulfides, sulfoxides or any suitable organic ligand or ligands if so desired. Phosphine oxides, phosphines, amines, amino acids or other nitrogen or phosphorous containing compounds and suitable organic ligands generally undergo quaternization in the presence of methyl iodide at elevated temperatures to yield salts which maintain elevated iodide anion concentration in the reaction mixture. The iodide salt stabilizer/co-promoters are thus defined by their ability to maintain elevated iodide anion levels, rather than by the form in which they are added to the system. One way of introducing iodide salt co-promoters is by incorporating suitable moieties into a rhodium catalyst system or complex as cations or ligands (typically monodentate or bidentate ligands) associated with rhodium added to the reaction mixture. Under carbonylation conditions in the presence of methyl iodide, these complexes decompose and/or quaternize to provide elevated levels of iodide anions. In this regard, the following Chinese References are of particular interest: Chinese Publication CN1345631; Application No. 00124639.9; Chinese Publication No. CN1105603; Application No. 94100505.4; and Chinese Publication No. CN1349855; Application No. 00130033.4. Suitable rhodium catatlyst complexes which provide iodide salt co-promoter thus include complexes having the following structures:

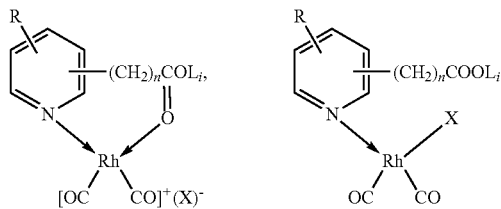

wherein R is H, or a carboxyl-containing hydrocarbon derivative; $(X^-)$ is $BPh_4^-$, $BF_4^-$, or $CH_3COO^-$; X is I, Cl, or Br; and n=0, 1, or 2. Other compounds useful as iodide salt co-promoters include pyridine derivatives such as:

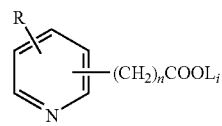

wherein R is H, or a carboxyl-containing hydrocarbon derivative, and n is 0, 1, or 2. Preferably, R is H, or e.g., lithium pyridine-2-formate, lithium pyridine-3-formate, lithium pyridine-4-formate, lithium pyridine-2-acetate, lithium pyridine-3-acetate, lithium pyridine-4-acetate, or lithium pyridine-3-propionate. One of skill in the art will appreciate that a great many other components may be used as iodide salt co-promoters.

An iridium catalyst in the liquid carbonylation reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO_2)]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in the following U.S. Pat. Nos. 5,942,460; 5,932,764; 5,883,295; 5,877,348; 5,877,347 and 5,696,284, the disclosures of which are hereby incorporated by reference into this application as if set forth in their entirety.

Methyl iodide is used as the promoter, although the selection of promoter is not critical to the operation of the present invention. Preferably, the concentration of methyl iodide in the liquid reaction composition is in the range 1 to 50% by weight, preferably 2 to 30% by weight.

The promoter may be combined with a salt stabilizer/co-promoter compound, especially in connection with rhodium catalyzed systems. These promoters may include salts of a metal of Group IA or Group IIA, or a quaternary ammonium or phosphonium salt or their precursors as described above. Particularly preferred are iodide or acetate salts, e.g., lithium iodide or lithium acetate.

Other promoters and co-promoters may be used as part of the catalytic system of the present invention as described in European Patent Publication EP 0 849 248, the disclosure of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of [0.5 to 15]:1, preferably [2 to 10]:1, more preferably [2 to 7.5]:1. A suitable promoter concentration is 400 to 5000 ppm.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water gas shift reaction is preferably kept low, for example, less than 1 Bar partial pressure, as its presence may result in the formation of hydrogenation products. The partial pressure of carbon monoxide in the reaction is suitably in the range 1 to 70 bar, preferably 1 to 35 bar, and most preferably 1 to 15 bar.

Acetic acid is typically included in the reaction mixture as the solvent for the reaction.

Suitable reactive derivatives of methanol include methyl acetate, dimethyl ether, methyl formate and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range 0.5 to 70% by weight, preferably 0.5 to 50% by weight, more preferably 1 to 35% by weight and most preferably 1-20% by weight, in the case of rhodium catalyzed systems, 1-10% by weight.

The carbonylation process in the primary reactor and pre-flash/post reactor vessel may be operated on a batch or semi-continuous basis, but preferably in a continuous mode. The pressure of the carbonylation reaction in the primary reactor is generally in the range 145 psi to 2900 psi (10 to 200 bar), preferably 145 psi to 1450 psi (10 to 100 bar), most preferably 217 psi to 725 psi (15 to 50 bar), for example about 400 psi (28 bar). Pressure in the pre-flash/post reactor vessel is reduced in many cases by from 10 to 40% of the primary reactor pressure, corresponding to a pressure reduction of approximately 40 psi. The pre-flash/post reactor vessel generally operates at a pressure of from about 160 psig to about 400 psig. The flash vessel is typically operated at a pressure within the range of about 14 to about 100 psig. The primary and pre-flash/post reactor vessels are operated at comparable temperatures. The temperature of the carbonylation reaction is suitably in the range 212° F. to 572° F. (100 to 300° C.), preferably in the range 302° F. to 428° F. (150 to 220° C.), for example about 370° F. (188° C.). Referring to FIG. 1, suitable pressures and compositions in the various pieces of equipment and streams are as follows:

Equipment
  12—carbonylation reaction pressure=300-500 psig, preferably 350-450 psig
  14—Preflasher/Post reactor pressure=200-450 psig, preferably 300-400 psig (always lower pressure than reactor 12)
  16—Flasher pressure=0-100 psig, preferably 15-45 psig
  52—vent scrubber pressure=5 to 500 psig, preferably 5-100 psig, more preferably 10-50 psig Streams
  30—comprising MeI, MeAc, CO
  34—comprising HAc, Rh, H2O, dissolved gases (CO/$CO_2$) and lower concentrations of MeAc and MeI than stream 24
  26—comprising CO, H2, CO2, CH4
  48—comprising non-condensable gases and MeI
  54—comprising primarily non-condensable gases with lower concentrations of MeI than stream 30

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition.

It is thus seen the pre-flasher/post reactor vessel is operated at a pressure of at least 5, 10, 15, 20, 25 or 30 psi lower than the pressure of the reactor vessel in various embodiments. So also, the Group VIII metal catalyst is a homogenous rhodium catalyst and is present in the reaction mixture at a concentration of from about 300 ppm to about 5,000 ppm by weight of the reaction mixture, while the amount of water in the reaction mixture in the reactor vessel is maintained at a level of from 0.1% by weight to 10% by weight of the reaction mixture and the reaction mixture further comprises an iodide salt stabilizer/co-promoter. Alternatively, the amount of water in the reaction mixture in the reactor vessel is maintained at a level of from 0.5% by weight to 8% by weight of the reaction mixture and the reaction mixture further comprises an iodide salt stabilizer/co-promoter or the amount of water in the reaction mixture in the reactor vessel is maintained at a level of from 0.5% by weight to 5% by weight of the reaction mixture and the reaction mixture further comprises an iodide salt stabilizer/co-promoter. In some preferred cases, the amount of water in the reaction mixture in the reactor vessel is maintained at a level of from 0.5% by weight to 3% by weight of the reaction mixture and the reaction mixture further comprises an iodide salt stabilizer/co-promoter, while the iodide salt stabilizer/co-promoter is present in an amount that generates and maintains an iodide anion concentration of from about 2 weight % to about 20 weight % of the reaction mixture in the reactor vessel such as wherein the iodide salt stabilizer/co-promoter is present in an amount that generates and maintains an iodide anion concentration of from about 5 weight % to about 17.5 weight % of the reaction mixture in the reactor vessel.

The iodide salt stabilizer/co-promoter is sometimes a mixture of iodide salts and/or the iodide salt stabilizer/co-promoter is provided to the reaction mixture in non-ionic form.

The Group VIII metal catalyst may be a homogenous iridium catalyst and the amount of water in the reaction mixture in the reactor vessel may be maintained at a level of from 3% by weight to 8% by weight of the reaction mixture while the the amount of methyl iodide in the reaction mixture in the reactor vessel is maintained at a level of from 2% by weight to 8% by weight of the reaction mixture and the amount of methyl acetate in the reaction mixture is maintained in the reactor vessel at a level of from 10% by weight to 20% by weight of the reaction mixture.

In one preferred aspect, carbon monoxide is sparged to the pre-flasher/post reactor vessel by way of a vent stream from the reactor. In another preferred aspect, the light ends from the pre-flasher/post reactor vessel are vented to a low pressure scrubber.

Typically, methyl acetate in the reaction mixture is consumed in the pre-flasher/post reactor vessel to a level at least 25% lower than the concentration of methyl acetate in the reaction mixture in the reaction vessel; sometimes the methyl acetate in the reaction mixture is consumed in the pre-flasher/post reactor vessel to a level at least 50% lower than the concentration of methyl acetate in the reaction mixture in the reaction vessel.

In another aspect of the invention, there is provided a carbonylation system for producing acetic acid comprising: (a) a reactor vessel adapted for carbonylating methanol or its reactive derivatives with carbon monoxide in the presence of a Group VIII metal catalyst and methyl iodide promoter in a liquid reaction mixture including acetic acid, water, methyl acetate and methyl iodide, the reactor being operated at a reaction pressure of from 300 psig to 500 psig; (b) a pre-flasher/post reactor vessel coupled to the reactor adapted to receive liquid reaction mixture forwarded thereto from the reactor, the pre-flasher/post reactor vessel being operated at a pressure of from 200 psig to 450 psig, with the proviso that the pressure in the pre-flasher/post reactor is at least 5 psi lower than the pressure in the reactor vessel and wherein the composition and conditions in the pre-flasher/post vessel are such that light ends are provided to a pre-flasher/post reactor vessel vent and a pre-flash mixture which is enriched in acetic acid and diminished in methyl iodide and methyl acetate as compared with the reaction mixture is formed; (c) a scrubber coupled to the vent of the pre-flasher/post reactor vessel adapted to recover light ends therefrom; (d) a flash vessel coupled to the pre-flasher/post reactor vessel adapted to receive liquid pre-flash mixture mixture forwarded thereto from the pre-flasher/post reactor vessel, the flasher vessel being operated at a pressure substantially lower than the pre-flasher/post reactor vessel pressure, the flash vessel being further adapted to flash a crude product stream from the pre-flash mixture and provide a recycle reaction mixture to the reactor; and (e) a purification section coupled to the flash vessel adapted to purify the crude product stream. The reactor may be operated at a pressure of from 350 psig to 450 psig while the pre-flasher/post reactor is operated at a pressure of from 300 to 400 psig, for example. Suitably, the pre-flasher/post reactor is operated at a pressure at least 15 psi lower than the reactor vessel while the flash vessel is operated at a pressure of from 0 psig to 100 psig such as wherein the flash vessel is operated at a pressure of from 15 psig to 45 psig. The vent scrubber is operated at a pressure of from 5 psig to 450 psig; more; suitably the vent scrubber is operated at a pressure of from 5 psig to 100 psig such as wherein the vent scrubber is operated at a pressure of from 10 psig to 50 psig.

In another preferred aspect of the invention, the pre-flasher/post reactor vessel is connected to a carbon monoxide source such as for example, where the carbon monoxide source comprises a vent stream from the reactor vessel.

Still further improvements include the system further comprising a pressure-reducing value coupling the vent stream of the reactor vessel and the pre-flasher/post reactor vessel and/or further comprising a pressure-reducing valve coupling the pre-flasher/post reactor vessel and the scrubber and/or further comprising a pressure-reducing valve coupling the pre-flasher/post reactor vessel and the flash vessel. In some cases, the reactor vessel is exclusively vented to the pre-flasher/post reactor vessel and the system is provided with a single, low pressure vent scrubber.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:
1. A method of making acetic acid comprising:
    (a) catalytically reacting methanol or a reactive derivative thereof with carbon monoxide in the presence of a homogeneous Group VIII metal catalyst and a methyl iodide promoter in a reactor vessel which contains a liquid reaction mixture including acetic acid, water, methyl acetate, methyl iodide and the homogeneous catalyst, the reactor vessel being operated at a reactor pressure;
    (b) withdrawing reaction mixture from the reaction vessel and feeding the withdrawn reaction mixture along with additional carbon monoxide to a pre-flasher/post reactor vessel operated at a reduced pressure below the reactor vessel pressure;
    (c) venting light ends in the pre-flasher vessel and concurrently consuming methyl acetate in the pre-flasher/post reactor vessel to produce a pre-flash mixture which is enriched in acetic acid and diminished in methyl iodide and methyl acetate as compared with the reaction mixture;
    (d) withdrawing the pre-flash reaction mixture from the pre-flasher/post reactor vessel and feeding the pre-flash mixture to a flash vessel;
    (e) flashing a crude acetic acid stream from the mixture in a flash vessel operated at a pressure substantially below the pressure of the pre-flasher/post reactor vessel;
    (f) recycling a post-flash residue from the flash vessel to the reactor vessel; and
    (g) purifying the crude product stream.

2. The method according to claim 1, wherein the pre-flasher/post reactor vessel is operated at a pressure of at least 5 psi lower than the pressure of the reactor vessel.

3. The method according to claim 1, wherein the pre-flasher/post reactor vessel is operated at a pressure of at least 10 psi lower than the pressure of the reactor vessel.

4. The method according to claim 1, wherein the pre-flasher/post reactor vessel is operated at a pressure of at least 15 psi lower than the pressure of the reactor vessel.

5. The method according to claim 1, wherein the pre-flasher/post reactor vessel is operated at a pressure of at least 20 psi lower than the pressure of the reactor vessel.

6. The method according to claim 1, wherein the pre-flasher/post reactor vessel is operated at a pressure of at least 25 psi lower than the pressure of the reactor vessel.

7. The method according to claim 1, wherein the pre-flasher/post reactor vessel is operated at a pressure of at least 30 psi lower than the pressure of the reactor vessel.

8. The carbonylation process according to claim 1, wherein the Group VIII metal catalyst is a homogenous rhodium catalyst and is present in the reaction mixture at a concentration of from about 300 ppm to about 5,000 ppm by weight of the reaction mixture.

9. The carbonylation process according to claim 8, wherein the amount of water in the reaction mixture in the reactor vessel is maintained at a level of from 0.1% by weight to 10% by weight of the reaction mixture and the reaction mixture further comprises an iodide salt stabilizer/co-promoter.

10. The carbonylation process according to claim 9, wherein the amount of water in the reaction mixture in the reactor vessel is maintained at a level of from 0.5% by weight to 8% by weight of the reaction mixture and the reaction mixture further comprises an iodide salt stabilizer/co-promoter.

11. The carbonylation process according to claim 9, wherein the amount of water in the reaction mixture in the reactor vessel is maintained at a level of from 0.5% by weight to 5% by weight of the reaction mixture and the reaction mixture further comprises an iodide salt stabilizer/co-promoter.

12. The carbonylation process according to claim 9, wherein the amount of water in the reaction mixture in the reactor vessel is maintained at a level of from 0.5% by weight to 3% by weight of the reaction mixture and the reaction mixture further comprises an iodide salt stabilizer/co-promoter.

13. The carbonylation process according to claim 9, wherein the iodide salt stabilizer/co-promoter is present in an amount that generates and maintains an iodide anion concentration of from about 2 weight % to about 20 weight % of the reaction mixture in the reactor vessel.

14. The carbonylation process according to claim 9, wherein the iodide salt stabilizer/co-promoter is present in an amount that generates and maintains an iodide anion concentration of from about 5 weight % to about 17.5 weight % of the reaction mixture in the reactor vessel.

15. The carbonylation process according to claim 9, wherein the iodide salt stabilizer/co-promoter is a mixture of iodide salts.

16. The carbonylation process according to claim 9, wherein the iodide salt stabilizer/co-promoter is provided to the reaction mixture in non-ionic form.

17. The carbonylation process according to claim 1, wherein the Group VIII metal catalyst is a homogenous iridium catalyst.

18. The carbonylation process according to claim 17, wherein the amount of water in the reaction mixture in the reactor vessel is maintained at a level of from 3% by weight to 8% by weight of the reaction mixture.

19. The carbonylation process according to claim 17, wherein the amount of methyl iodide in the reaction mixture in the reactor vessel is maintained at a level of from 2% by weight to 8% by weight of the reaction mixture.

20. The carbonylation process according to claim 17, wherein the amount of methyl acetate in the reaction mixture is maintained in the reactor vessel at a level of from 10% by weight to 20% by weight of the reaction mixture.

21. The method according to claim 1, wherein carbon monoxide is sparged to the pre-flasher/post reactor vessel by way of a vent stream from the reactor.

22. The method according to claim 1, wherein the light ends from the pre-flasher/post reactor vessel are vented to a low pressure scrubber.

23. The method according to claim 1, wherein methyl acetate in the reaction mixture is consumed in the pre-flasher/post reactor vessel to a level at least 25% lower than the concentration of methyl acetate in the reaction mixture in the reaction vessel.

24. The method according to claim 1, wherein methyl acetate in the reaction mixture is consumed in the pre-flasher/post reactor vessel to a level at least 50% lower than the concentration of methyl acetate in the reaction mixture in the reaction vessel.

* * * * *